United States Patent [19]

Gregg et al.

[11] Patent Number: 5,379,900
[45] Date of Patent: Jan. 10, 1995

[54] NEEDLE SHIELDING CUSHION KIT

[75] Inventors: Joseph J. Gregg, Hasbrouck Heights; Richard L. Griffith, III, Allendale, both of N.J.

[73] Assignee: Becton, Dickinson and Company, Franklin Lakes, N.J.

[21] Appl. No.: 101,156

[22] Filed: Aug. 3, 1993

[51] Int. Cl.6 .......................... B65D 71/00; B65D 6/04
[52] U.S. Cl. ..................... 206/571; 206/364; 206/560; 206/565; 211/70.6
[58] Field of Search ............... 206/571, 364, 365, 363, 206/366, 370, 560, 565; 211/70.6, 70.7

[56] References Cited

U.S. PATENT DOCUMENTS

| | | | |
|---|---|---|---|
| D. 252,342 | 7/1979 | Brady | 206/366 X |
| 4,485,919 | 12/1989 | Sandel | 206/370 |
| 4,523,679 | 6/1985 | Paikoff | 206/370 |
| 4,657,138 | 4/1987 | Watson | 206/366 |
| 4,974,728 | 12/1990 | Colton | 206/366 |
| 5,024,326 | 6/1991 | Sandel et al. | 206/366 |
| 5,201,430 | 4/1993 | Artzer | 211/70.6 |

*Primary Examiner*—Bryon P. Gehman
*Attorney, Agent, or Firm*—Vincent A. Castiglione

[57] ABSTRACT

A needle shielding cushion is provided with a generally planar base wall having a plurality of filaments projecting unitarily therefrom. The base wall defines cross-sectional dimensions which are greater than the length of a needle cannula used therewith. The filaments are dimensioned and disposed to releasably engage a needle cannula therebetween. An exposed needle cannula can be urged between the filaments after usage of the needle cannula and/or between sequential uses of the needle cannula.

11 Claims, 4 Drawing Sheets

NEEDLE SHIELDING CUSHION KIT

FIELD OF THE INVENTION

The present invention relates to a needle shielding cushion for preventing accidental contact with the sharply pointed tip of a needle cannula, and more particularly to a cushion for protectively surrounding the needle cannula in situations where a hypodermic syringe can be positioned between uses or cannot be safely discarded immediately after use.

DESCRIPTION OF THE PRIOR ART

Prior art hypodermic syringes are provided with rigid shields for protectively enclosing the needle cannula. A typical prior art needle shield is an elongate open-ended cap dimensioned to be telescoped over the needle cannula. The open end of the prior art needle shield is configured to engage the syringe barrel or the needle hub in a manner that will prevent accidental separation.

The needle shield typically is secured over the needle cannula prior to use of the hypodermic syringe. The health care worker then removes the needle shield and uses the hypodermic syringe to inject mediation into a patient or to extract bodily fluids from the patient. The used hypodermic syringe may be deposited in a sharps receptacle if such a receptacle is immediately available.

If a sharps collector is not readily available, the health care worker may attempt to reshield the needle. Needle sticks can occur as the health care worker attempts to telescope the small open end of a needle shield over the sharp tip of the used needle cannula. Hence, the prior art includes needle shields that are intended to prevent accidental needle sticks during reshielding. For example, some prior art needle shields include handles that enable the health care worker to hold the needle shield at a location offset from the longitudinal axes of the needle cannula. Other prior art needle shields include a base that permits the needle shield to be supported vertically with the open end up. The health care worker may then use only one hand to urge the needle cannula downwardly and into the upright needle shield. Still other prior art needle shields rely on a hinged interaction between the needle shield and the needle cannula to avoid the axial movement that could leak to needle sticks.

Although reshielding is not a recommended practice, the above-described prior art needle shields all offer some degree of effectiveness if the health care worker has ample time to use the needle shield in its prescribed manner. In many instances, however, hospital policy may not allow reshielding or the health care worker simply does not have the luxury of interrupting his or her care for the patient to shield a needle cannula. This is particularly true in emergency rooms or in other environments where health care services are being administered quickly and in rapid succession. In these situations, if a sharps collector is not readily available, the health care worker is likely to deposit the used and unshielded hypodermic syringe on a table or tray with the intention of properly disposing the used hypodermic syringe when time permits. As a result, the unshielded needle cannula may lie exposed in a position where an accidental stick can occur.

Re-shielding a hypodermic syringe also can be a problem in operating rooms. For example, anesthesia and certain medications often are administered in the operating room with a hypodermic syringe. Operating procedures may require the anesthesia or other medication to be administered incrementally in small doses over a period of time. Thus, the health care worker may inject a small amount of anesthesia into the patient, and then may deposit the hypodermic syringe on a work surface in the operating room for use a short time later. It is not practical to telescope a prior art needle shield over the needle cannula between these sequential uses of the hypodermic syringe. However, the exposed needle cannula of the hypodermic syringe poses a risk for accidental needle sticks as health care workers continuously manipulate, access and discard surgical tools and related equipment in the operating room.

SUMMARY OF THE INVENTION

The subject invention is directed to a cushion into which an elongate needle cannula may be safely received. The cushion may be unitarily molded from a thermoplastic material and may include a substantially rigid generally planar base which can be supported on a horizontal surface such as a table or procedural tray. The base may be thin and/or hollow to reduce the weight of the cushion. However, the base also should be sufficiently reinforced to prevent significant deflection. The width of the base preferably is greater than the length of the needle cannula.

The cushion further features a plurality of filaments or bristles projecting upwardly from the base. The filaments may be resiliently flexible and unitary with the base. Each filament or bristle may be tapered, with a major width adjacent the base and a minor width at locations remote from the base. With this configuration, distances between adjacent filaments at locations near the base may be less than or approximately equal to the width of the needle cannula to be shielded. However, distances between adjacent filaments at locations remote from the base may be greater than the width of the needle cannula. Thus, a needle cannula may readily be moved transversely to its own axis, toward the cushion and intermediate filaments of the cushion. The filaments will engage the needle cannula as the needle cannula approaches the base of the cushion. The base and the filaments of the cushion will prevent inadvertent contact with needle cannula while the hypodermic syringe is lying on the tray or table. The filaments also will prevent the hypodermic syringe from rolling or sliding across the tray. Additionally, the weight of the cushion, and the resilient forces exerted by the filaments on the needle cannula may be selected to keep the cushion engaged on the needle cannula when the hypodermic is lifted. Thus, gravitational forces exerted on the cushion may not be sufficient to overcome the engagement forces of the filaments on the needle cannula. The cushion should be sterile if the needle cannula will be used more than once so that the cushion will not contaminate the needle cannula.

The subject invention may further include a kit of medical devices to be used during certain procedures, such as the administration of anesthesia in an operating room. The kit may include a needle shielding cushion as described above. The kit may further include a hypodermic syringe with a needle cannula dimensioned to be safely received between the filaments and adjacent the base of the cushion. Gauze pads, disinfecting wipes, blades, tape, anesthesia and/or other equipment or supplies may be included in the kit, depending upon the intended end use of the kit. All of the elements of the kit may be supported on a tray and sealed in a protective wrap to protect sterility. The tray may then be employed to support the needle shielding cushion and the hypodermic syringe after each use.

The subject invention is desirable in that it enables a health care worker to at least temporarily shield a needle cannula by merely placing the hypodermic syringe on the table or tray with one hand such that the needle cannula is urged onto the cushion in a direction transverse to the axis of the needle cannula. The forces exerted by gravity and by the health care worker depositing the hypodermic syringe will cause the needle cannula to advance intermediate the filaments of the cushion. The base of the cushion will prevent accidental contact with the point of the needle cannula. The filaments will frictionally and/or resiliently engage the needle cannula to ensure that the hypodermic syringe and the cushion remain properly positioned relative to one another. The hypodermic syringe with the safely protected needle cannula may be at least temporarily retained on the table or tray in this safely protected manner. The health care worker may periodically access the needle cannula as an extended medical procedure is carded out. After each sequential use, the needle cannula may be re-positioned in the needle shielding cushion. The hypodermic syringe and cushion may then be deposited into a sharps collector at an appropriate and convenient time after the initial placement of the used hypodermic syringe on the cushion.

DETAILED DESCRIPTION OF THE PREFERRED EMBODIMENT

Figure 1:
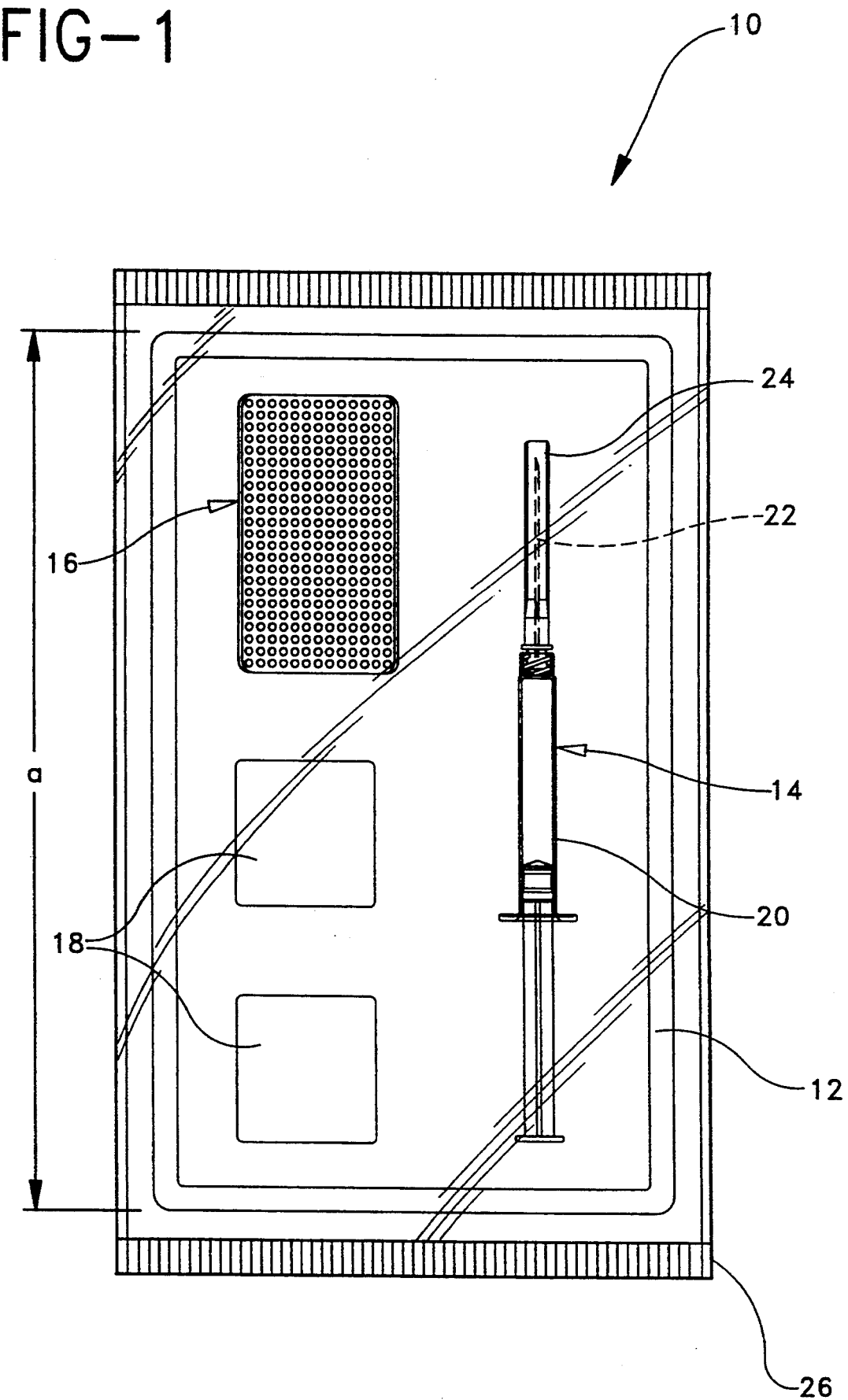
FIG. 1 is a top plan view of a kit of devices, including a hypodermic syringe and a needle shielding cushion in accordance with the subject invention.
Figure 2:
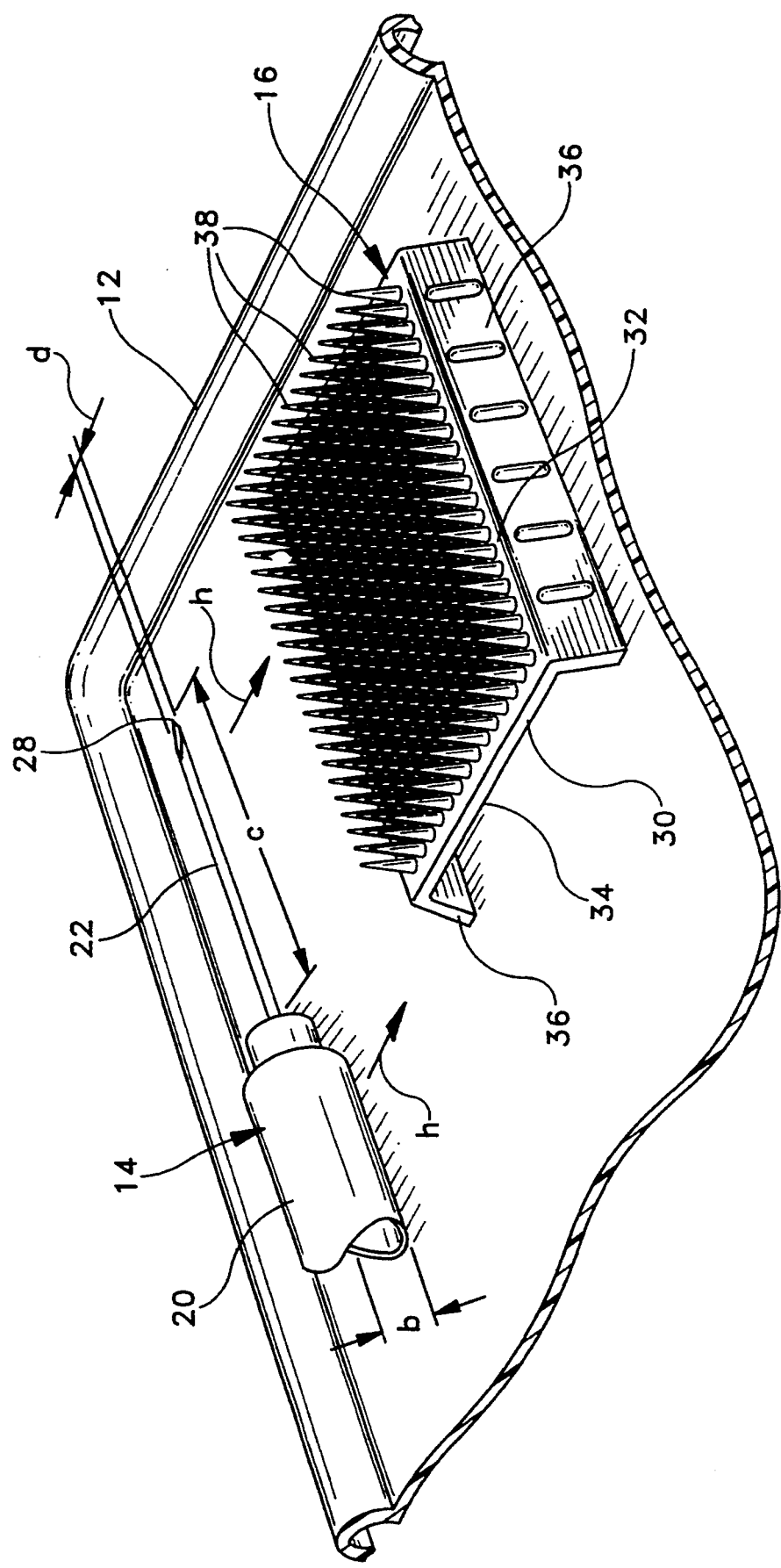
FIG. 2 is an exploded perspective view showing a hypodermic syringe in proximity to the needle shielding cushion of the subject invention.
Figure 3:
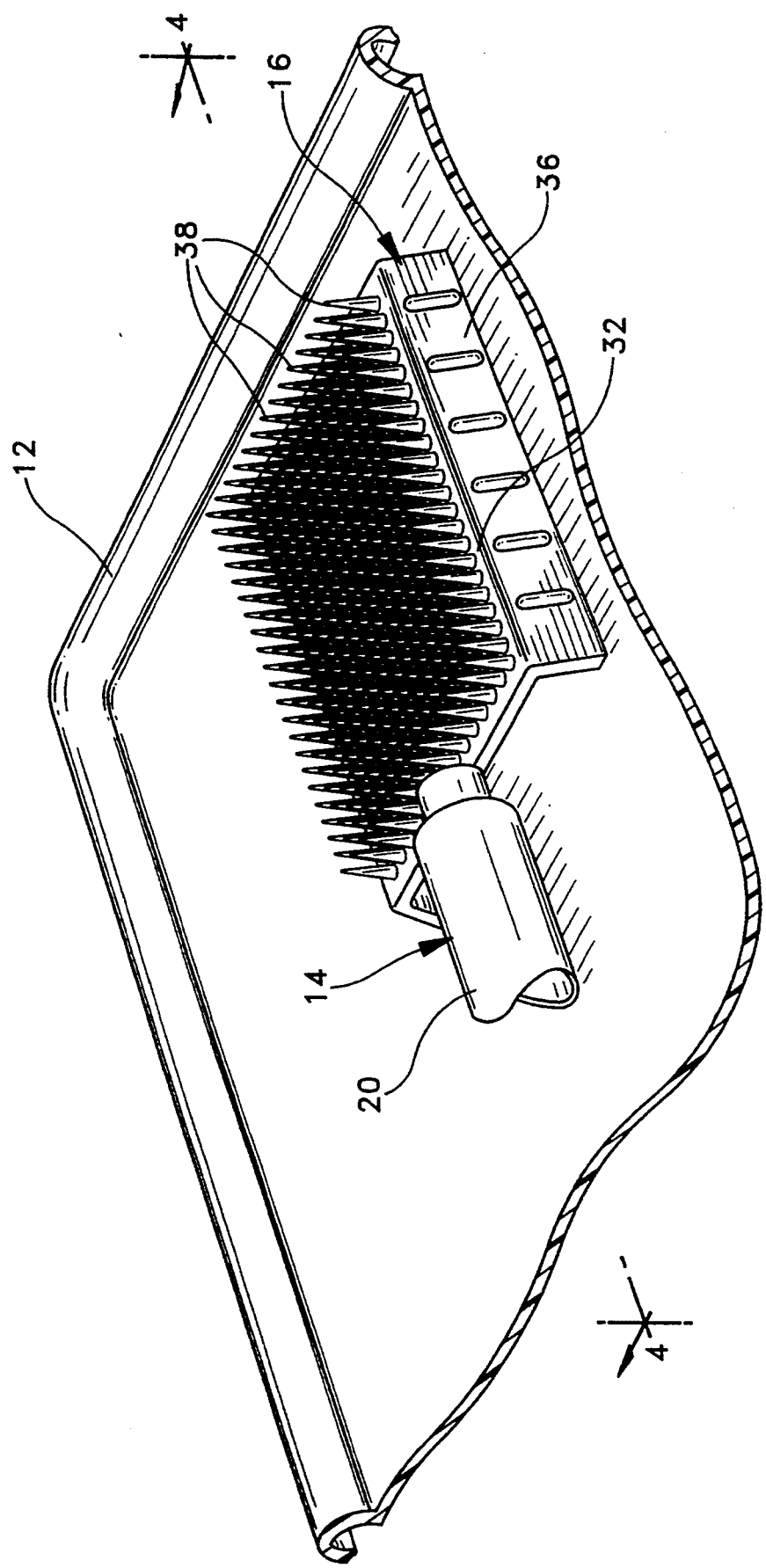
FIG. 3 is a perspective view showing the cushion protectively engaging the needle cannula of the syringe.
Figure 4:
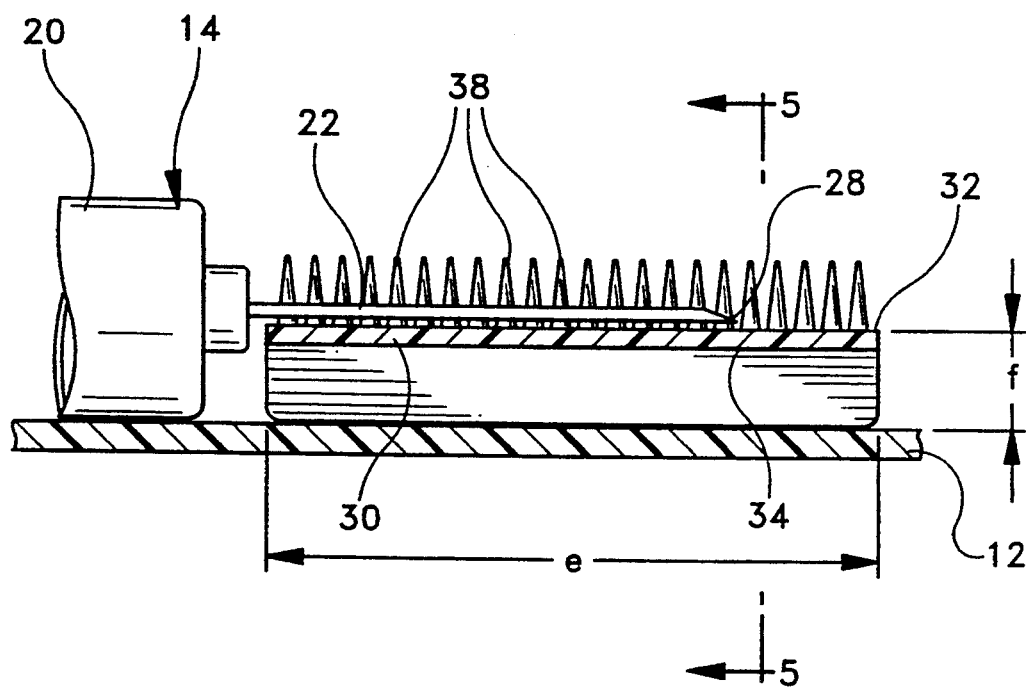
FIG. 4 is a cross-sectional view taken along line 4—4 of FIG. 3.
Figure 5:
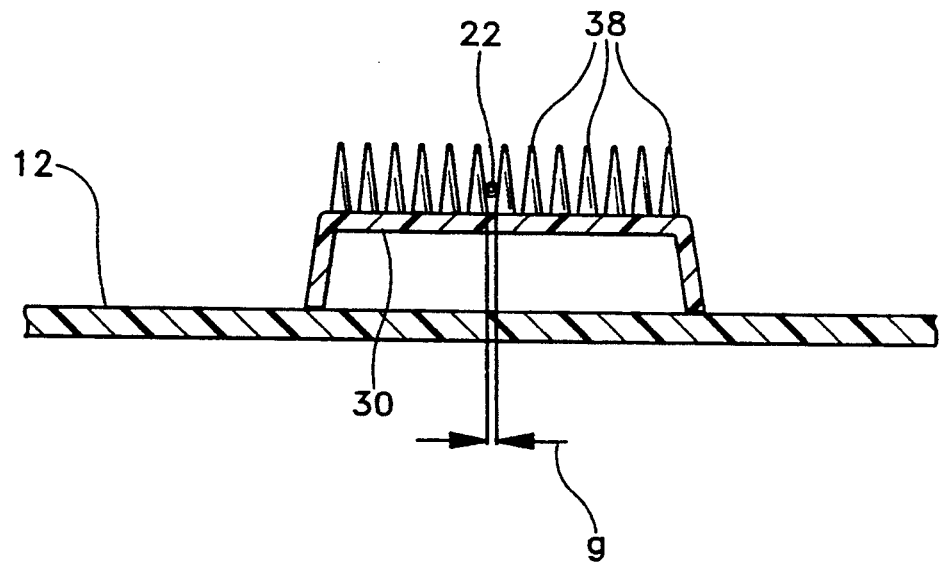
FIG. 5 is a cross-sectional view taken along line 5—5 of FIG. 4.

A kit of medical equipment in accordance with the subject invention is identified generally by the numeral 10 in FIG. 1. Kit 10 includes a rigid generally planar tray 12 having a length "a". Tray 12 supports a hypodermic syringe 14, a needle shielding cushion 16 and other devices or articles identified generally by the numeral 18. Equipment 18 will vary in accordance with the intended use for the kit. For example, device 18 in kit 10 may include gauze pads, wipes, anesthesia or medicine to be injected.

Hypodermic syringe 14 includes a syringe barrel 20, a needle cannula 22 affixed to syringe barrel 20 and a needle shield 24 protectively telescoped over needle cannula 22. An outer wrapper 26 covers tray 12 and everything supported thereon and protects the sterility of the kit.

Kit 10 is intended for a particular medical procedure, such as procedures requiring anesthesia or medication to be injected incrementally over time. Wrapper 26 may be opened and the health care worker may remove and use syringe 14 in the standard manner. Alter each injection of an incremental dose, the health care worker will re-position hypodermic syringe 14 on tray 12 as explained herein.

As shown more clearly in FIGS. 2–5, syringe barrel 20 is generally cylindrical and defines a radius "b". Needle cannula 22 includes a sharp point 28 defining the extreme distal tip of hypodermic syringe 14. Point 28 of needle cannula 22 is spaced a distance "c" from syringe barrel 20 to define the overall length of needle cannula 22. Needle cannula 20 further defines a diameter "d".

Needle shielding cushion 16 includes a generally planar base wall 30 having opposed top and bottom surfaces 32 and 34. Base wall 30 defines a length "e", measured in the plane of the base wall 30, which is greater than the length "c" of needle cannula 22. Base wall 30 is formed from a substantially rigid thermoplastic material that is preferably selected to resist or prevent puncture by point 28 of needle cannula 22. A plurality of support walls 36 projecting downwardly from bottom surface 34 of base wall 30 are preferably provided to enable base wall 30 to be supported in generally spaced parallel relationship to tray 12. Support walls 36 are dimensioned to keep top surface 32 of base wall 30 a distance "f" from tray 12 on which needle shielding cushion 16 is supported. Dimension "f" preferably is approximately equal to or slightly less than radius "b" of syringe barrel 20. Support walls 36 are preferably spaced from one another adjacent peripheral regions of base wall 30 to enable a health care worker to insert a thumb or forefinger between base wall 30 and tray 12 for lifting needle shielding cushion 16.

Needle shielding cushion 16 further includes a plurality of rigid resiliently flexible filaments 38 which project from top surface 32 of base wall 30 and substantially orthogonal thereto. In this preferred embodiment, each filament 38 is of tapered generally conical shape defining a major dimension at locations substantially adjacent base wall 30. As shown most clearly in FIG. 5, filaments 38 are spaced from one another by a minor distance "g" at locations on filaments 38 in proximity to base wall 30. Distance "g" between adjacent filaments 38 is preferably less than or approximately equal to diameter "c" of needle cannula 24. However, having filaments 38 spaced at a dimension greater than "g" is within the purview of the invention. Staggering the filaments rather than placing them in precise rows and columns will allow greater filament spacing.

Needle shielding cushion 16 may be placed on the tray 12 with filaments 38 projecting upwardly. Hypodermic syringe 14 may be used to incrementally administer an appropriate dose of medication or anesthesia to a patient. After each use, hypodermic syringe 12 may be moved transversely to its longitudinal axis, as shown by arrow "h" in FIG. 2, and may be deposited on tray 12 with needle cannula 22 being engaged between filaments 38 of needle shielding cushion 16. Length "e" of base wall 30 of needle shielding cushion 16 is greater than length "c" of needle cannula 22. Thus, base wall 30 positively prevents accidental needle sticks between incrementally administered doses of medicine or anesthesia. More particularly, point 28 of needle cannula 22 is safely protected between filaments 38 and by rigid base wall 30. Filaments 38 prevent hypodermic syringe 14 from rolling or sliding free of needle shielding cushion 16. Additionally dimensions, spacing and resilient characteristics of filaments 38 can be selected to ensure that cushion 16 remains engaged with needle cannula 22 even when hypodermic syringe 14 is lifted from tray 12.

This latter feature may not be desirable for situations where the hypodermic syringe is subject to plural sequential uses, but may be desirable for emergency rooms where a quick one-time protection of the needle cannula is needed prior to depositing the hypodermic syringe in a sharps receptacle.

What is claimed is:

1. A prepackaged kit of medical articles comprising a hypodermic syringe having a sharply pointed needle cannula having a diameter and a needle shielding cushion, said cushion comprising a substantially planar base wall and upstanding filaments extending in a generally orthogonal direction from said base wall, said filaments having an orthogonal extent greater than the diameter of said needle cannula, said filaments being spaced from one another by distances to enable said needle cannula to be urged transversely between a plurality of said filaments, wherein when said needle cannula is substantially horizontally embedded between said plurality of filaments, said plurality of filaments and said base wall act to prevent accidental contact with said needle cannula.

2. The kit of claim 1, wherein said filaments are spaced from one another a distance for frictionally engaging said needle cannula when said needle cannula is substantially adjacent said base wall and between a plurality of adjacent filaments.

3. The kit of claim 1, wherein a plurality of said filaments are spaced so that: the distance between said filaments is less than the diameter of said needle cannula.

4. The kit of claim 1, wherein a plurality of said filaments are of generally conical shape defining a major cross-sectional dimension substantially adjacent the base wall.

5. The kit of claim 1, further comprising a tray for supporting said medical articles prior to usage and for supporting said needle shielding cushion and said needle cannula engaged therewith after use of said hypodermic syringe.

6. The kit of claim 1, wherein said needle cannula defines a length, said substantially planar base wall of said needle shielding cushion defining a cross-sectional dimension measured generally parallel to the plane of said base wall, said crosssectional dimension of said base wall being greater than said length of said needle cannula.

7. The kit of claim 1, wherein said hypodermic syringe includes a substantially cylindrical syringe barrel further comprising support walls radius, said base wall defining a extending below the base wall a distance approximately equal to said radius of said syringe barrel, such that said needle cannula is approximately parallel to and adjacent said base wall when said needle cannula is embedded between said plurality of filaments and said base wall and said syringe barrel are resting on a common plane supporting surface.

8. The kit of claim 1 wherein said filaments are resiliently flexible for releasably engaging a syringe barrel transversely urged between said filaments.

9. The kit of claim 1, wherein said needle shielding cushion is of unitary construction.

10. The kit of claim 1, wherein said needle shielding cushion is made of thermoplastic material.

11. The kit of claim 1, wherein said articles are sterile.

* * * * *